US006972349B1

(12) United States Patent
Vance

(10) Patent No.: US 6,972,349 B1
(45) Date of Patent: Dec. 6, 2005

(54) CONTROL OF POST-TRANSCRIPTIONAL GENE SILENCING IN PLANTS

(75) Inventor: Vicki Vance, Columbia, SC (US)

(73) Assignee: University of South Carolina, Columbia, SC (US)

( * ) Notice: Subject to any disclaimer, the term of this patent is extended or adjusted under 35 U.S.C. 154(b) by 490 days.

(21) Appl. No.: 09/711,334

(22) Filed: Nov. 9, 2000

Related U.S. Application Data

(60) Provisional application No. 60/237,432, filed on Oct. 3, 2000, and provisional application No. 60/165,199, filed on Nov. 12, 1999.

(51) Int. Cl.[7] .......................... C12N 15/82; C12N 15/90; C12N 15/29
(52) U.S. Cl. ........................................ 800/278; 800/279
(58) Field of Search ............................ 435/69.1, 69.7, 435/410, 419, 468; 800/278, 288, 295, 298; 536/23.6

(56) References Cited

FOREIGN PATENT DOCUMENTS

WO        0138512      5/2001    ........... C12N/15/00

OTHER PUBLICATIONS

Anandalakshmi et al., Science, Oct. 2000, vol. 290, pp. 142–144.*
Bingham, P. M. (1997) "Cosuppression comes to the animals," Cell 90:385–387.
Engel, M., Seifert, M., Theisinger, B., Seyfert, U., and Welter, C. (1998) "Glyceraldehyde3–phosphate dehydrogenase and NM23–HI/nucleoside diphosphate kinase A. Two old enzymes combine for the novel Nm23 protein phosphotransferase function," J. Biol. Chem. 273:2005–20065.
Ruiz, M.T., Voinnet, O., and Baulcombe, D.C. (1998) "Initiation and maintenance of virus induced gene silencing," Plant Cell 10:937–946.
Kumagai, M.H., Donson, J., Della–Cioppa, G., Harvey, D., Hanley, K., and Grill, L.K. (1995) "Cytoplasmic inhibition of carotenoid biosynthesis with virus–derived RNA," Proc. Natl. Acad. Sci USA 92:1679–1683.
Kennerdell, J.R. and Carthew, R. W. (1998) "Use of dsRNA–mediated genetic interference to demonstrate that frizzled and frizzled 2 act in the wingless pathway," Cell 95:1017–1026.
Jones, A.L., Thomas, C.L. and Maule, A.J. (1998) "De novo methylation and cosuppression induced by a cytoplasmically replicating plant RNA virus," EMBO J. 17:6385–6393.
Ruiz, F., Vayssie, L., Klotz, C., Sperling, L., and Madeddu, L. (1998) "Homology–dependent gene silencing in Paramecium," Mol. Biol. Cell 9:931–943.
Metzlaff, M., O'Dell, M., Cluster, P.D., and Flavell, R.B. (1997) "RNA–mediated RNA degradation and chalcone synthase A silencing in Petunia," Cell 88:845–854.

Montgomery, M. K. and Fire, A. (1998) "Double stranded RNA as a mediator in sequence specific genetic silencing and co–suppression," Trends Genet. 14:255–258.
Fire, A., Xu, S., Montgomery, M.K., Kostas, S.A., Driver, S.E. and Mello, C.C. (1998) "Potent and specific genetic interference by double stranded RNA in Caenorhabditis elegens.," Nature 391:806–811.
Sharp, Phillip.A. (1999) "RNAi and double–strand RNA," Genes & Dev., 13:139–141.
Wiammy, F. and M. Zernicka–Goetz (2000) "Specific interference with gene function by double–stranded RNA in early mouse development," Nature Cell. Biol. 2:70–75.
Depicker, A. and Van Montagu, M. (1997) "Post–transcriptional gene silencing in plants," Curr. Opin. Cell Biol. 9:373–382.
Al–Kaff. N..S., Covey, S.N., Kreike, M.M., Page, A.M., Pinder. R. & Dale. P.J. (1998) "Transcriptional and post transcriptional plant gene silencing in response to a pathogen," Science 279:2113–2115.
Baulcombe, D.C. (1999) "Fast forward genetics based on virus–induced gene silencing," Curr. Opin. Plant Biol. 2:109–113.
Brigneti, G., Voinnet, O., Li, W.–X., Ji, L.–H., Ding, S.–W. and Baulcombe, D. (1998) "Viral pathogenicity determinants are suppressors of transgene silencing in Nicotiana benthamiana," EMBO J. 17:6739–6746.
Waterhouse, P.M., Graham, NW. and Wang, M. (1998) "Virus resistance and gene silencing in plants can be induced by simultaneous expression of sense and antisense RNA," Proc. Natl. Acad. Sci. USA 95:13959–13964.
Grant, S. (1999) "Dissecting the mechanisms of post transcriptional gene silencing: Divide and conquer," Cell 96:303–306.
Sharp, P .A. and P.D. Zamore (2000) "RNA Interference," Science 287:2431–2432.
Kasschau, K.D. and Carrington, J.C. (1998) "A counterdefensive strategy of plant viruses: Suppression of post transcriptional gene silencing." Cell 95:461–470.
Palauqui, J.C., T. Elmayan, F. Dorlhac de Borne, P. Crete, C. Charles and H. Vaucheret (1996) "Frequencies, Timing, and Spatial Patterns of Co–suppression of Nitrate Reductase and Nitrite Reductase in Transgenic Tobacco Plants," Plant Physiol. 112:1447–1456.
Ratcliff, F., Harrison, B., and Baulcombe, D. (1997) "A similarity between viral defense and gene silencing in plants," Science 276:1558–1560.

(Continued)

Primary Examiner—Ashwin Mehta
(74) Attorney, Agent, or Firm—Alston & Bird LLP

(57) ABSTRACT

Calmodulin-like polypeptides named rgs-CaM are disclosed. cDNAs coding rgs-CaM are also provided. In addition, methods of using rgs-CaM cDNAs and polypeptides for modulating gene expression in plants are also provided.

13 Claims, 5 Drawing Sheets

OTHER PUBLICATIONS

Vance, V.B., Berger, P.H., Carrington J.C., Hunt, A.G., and Shi, X.M. (1995) "5' proximal potyviral sequences mediate potato virus X/potyviral synergistic disease in transgenic tobacco," *Virology* 206:583–590.

Vance, V.B. (1991) "Replication of potato virus X RNA is altered in coinfections with potato virus Y," *Virology* 182 486–494.

Anandalakshmi, R., Pruss, G.J., G E, X., Marathe, R., Mallory, A.C., Smith, T.H. and Vance, V.B. (1998) "A viral suppressor of gene silencing in plants," *Proc. Natl. Acad. Sci. USA* 95:13079–13084.

Pruss, G., Ge, X., Shi, X.M., Camngton, J. C., and Vance, V.B. (1997) "Plant viral synergism: the potyviral genome encodes a broad–range pathogenicity enhancer that transactivates replication of heterologous viruses," *Plant Cell* 9:1–11.

Anandalakshmi, R., Marathe, R., Ge, X., Herr, Jr., J.M., Mau, C., Mallory, A., Pruss, G., Bowman, L., Vance, V.B. (2000) "A calmodulin–related protein that suppresses post-transcriptional gene silencing in plants," *Science* 290:142–144.

Shi, X.M., Miller, H., Verchot, J., Carrington, J.C., Vance, V.B. (1997) "Mutations in the region encoding the central domain of helper component–proteinase (HC–Pro) eliminate potato virus X/potyviral synergism," *Virology* 231:35–42.

Marathe, R., Anandalakshmi, R., Smith, T.H., Pruss, G.J., Vance, V.B. (2000) "RNA viruses as inducers, suppressors and targets of post–transcriptional gene silencing," *Plant Mol. Biol.* 43:295–306.

Dearolf, C.R., Hersperger, E. and Sheam A. (1988) "Developmental consequences of awdb3. a cell–autonomous lethal mutation of *Drosophila* induced by hybrid dysgenesis," *Dev. Biol.* 129:159–168.

Postel, E. H., Berbench, S.J., Flint, S.J., and Ferrone, C.A. (1993) "Human c–myc transcription factor PuF identified as nm–23–H2 nucleoside diphosphate kinase, a candidate suppressor of tumor metastasis," *Science* 261:478–480.

Palauqui, J.C. and H. Vaucheret (1995) "Field Trial Analysis of Nitrate Reductase Co–suppression: A comparative Study of 38 Combinations of Transgene Loci," *Plant Mol. Biol.* 29:149–159.

Fire, A. (1999) "RNA–triggered gene silencing", *Trends Genet.* 15:358–363.

Matzke, M.A. and Matzke, A.J.M. (1995) "Homology–dependent gene silencing in transgenic plants: what does it really tell us," *Trends in Genetics* 19, 1–3.

Howlett, A.R., Peterson, O.W., Steeg, P.S., and Bissell, M.J. (1994) "A novel function for the nm23–H1 gene: overexpression in human breast carcinoma cells leads to the formation of basement membrane and growth arrest." *J. Natl. Cancer Inst.* 86:1838–1844.

Carrington et al. (1990) "Expression of potyviral polyproteins in transgenic plants reveals three proteolytic activities required for complete processing". *EMBO, J.* 9:1347–1353.

de la Rosa, A., Williams, R.L. and Steeg, P.S. (1995) "Nm23/nucleoside diphosphate kinase: toward a structural and biochemical understanding of its biological functions." *Bioassays* 17:53–62.

* cited by examiner

CONTROL OF POST-TRANSCRIPTIONAL GENE SILENCING IN PLANTS

CROSS-REFERENCE TO A RELATED APPLICATION

This application claims the benefit of U.S. Provisional Applications Ser. Nos. 60/165,199, filed Nov. 12, 1999; and 60/237,432, filed Oct. 3, 2000.

The subject invention was made with government support under a research project supported by USDA NRI Competitive Grants, Grant No. 97022709. The government has certain rights in this invention.

BACKGROUND OF THE INVENTION

Post-transcriptional gene silencing (PTGS) is an ancient eukaryotic regulatory mechanism (Bingham, 1997) in which a particular RNA sequence is targeted and destroyed. The process may be triggered when multiple copies of a transgene (or a transgene and a homologous endogenous gene) are present in the same genome (for recent reviews of PTGS see Depicker and Van Montagu, 1997; Grant, 1999). Double stranded RNA induces PTGS in many systems (Metzlaff et al., 1997; Montgomery and Fire, 1998; Waterhouse et al., 1999) and, in plants, it can also be triggered by cytoplasmically replicating viruses many of which produce double stranded RNA replication intermediates (Baulcombe, 1999; Kumagai et al., 1995; Ruiz et al., 1998). Once the mechanism has been triggered, any homologous RNA is degraded whether it is transcribed from the transgene, the endogenous gene or from the viral RNA. The fact that plant viruses can act both as inducers and as targets of post-transcriptional gene silencing (AJ-Kaff et al., 1998; Matzke and Matzke, 1995; Ratcliff et al., 1997) has led to the idea that PTGS may have evolved as an antiviral defense mechanism in plants. The related processes in other eukaryotic organisms may serve a similar function.

If PTGS is an antiviral defense mechanism in plants, then it is not surprising that some plant viruses have evolved a counter-defense. Our recent work and that of others has identified a plant viral protein, HC-Pro, that interferes with the induction of post-transcriptional gene silencing (Anandalakshmi et al., 1998; Brigneti et al., 1998; Kasschau and Carrington, 1998). This result further supports the idea that PTGS may be linked to natural antiviral resistance systems in plants, and opens the door to a new approach to understanding gene silencing in plants.

The identification of a viral suppressor of PTGS stems from studies of synergistic viral disease, in which coinfection with two heterologous viruses leads to much more severe symptoms than does infection with either virus alone. Many such synergistic diseases involve a member of the potyvirus group of plant viruses (Vance, 1991; Vance et al., 1995). Previously, it was found that transgenic plants expressing the 5' proximal region of the tobacco etch potyviral (TEV) genome (termed the P1/HC-Pro sequence) develop synergistic disease when infected with any of a broad range of plant viruses (Pruss et al., 1997). This result suggested that expression of the P1/HC-Pro sequence might interfere with a general antiviral system in plants, thereby permitting viruses to accumulate beyond the normal host mediated limits. The general antiviral system was hypothesized to be post-transcriptional gene silencing (Pruss et al., 1997). To test this hypothesis, the effect of P1/HC-Pro expression on post-transcriptional gene silencing was tested in two different silencing systems. The results indicate that P1/HC-Pro acts as a suppressor of both transgene-induced (Anandalakshmi et al., 1998; Kasschau and Carrington, 1998) and virus-induced gene silencing (Anandalakshmi et al., 1998; Brigneti et al., 1998). Further experiments indicated that the suppression of PTGS is mediated by the HC-Pro protein, that the RNA is not sufficient for suppression and that the P1 protein may act as a nonessential accessory protein in the suppression (Anandalakshmi et al., 1998; Brigneti et al., 1998).

Expression of P1/HC-Pro in transgenic plants confers a number of phenotypes, some potentially useful, others detrimental. As discussed above, P1/HC-Pro interferes with post-transcriptional gene silencing. This phenotype is potentially useful. PTGS limits the level of expression from transgenes and is a serious problem in many biotechnology applications, and HC-Pro can be used to directly counter PTGS. However, suppression of PTGS is not the only process affected by HC-Pro. The P1/HC-Pro transgenic plants have an altered response to viral plant pathogens (and possibly to other pathogens as well). Our early experiments showed that P1/HC-Pro-expressing transgenics respond to infection with potato virus X or tobacco mosaic virus with a systemic necrosis (Pruss et al., 1997). However, in other cases the response of these plants to a viral pathogen resembles systemic acquired resistance (SAR). Under conditions where the N resistance gene of tobacco is active, the plants respond to TMV inoculation with fewer and smaller lesions than wild control plants (the classic SAR response). The same lines are completely resistant to infection with tomato ringspot nepovirus, although the control plants are susceptible. The mechanism of this induced resistance is unknown. Expression of P1/HC-Pro in transgenic plants also confers several unique developmental characteristics. The first leaves of the germinating plants are pointed rather than being rounded (the pointed character is a mature leaf character while rounded is the appropriate immature character). The plants grow slowly with reduced root biomass, and a differentiated tumor develops at the junction of the stem and the root. Finally, the flowers show delayed and reduced pigmentation. This result suggests that PTGS is used by plants as one aspect of developmental gene regulation.

To fully utilize transgenic plants, the mechanisms behind gene expression and suppression need to be controlled. In particular, methods for modulating gene expression in plants are needed.

BRIEF SUMMARY OF THE INVENTION

We have identified a number of plant proteins that interact with HC-Pro in the yeast two-hybrid system. One of these HC-Pro-interacting proteins, rgs-CaM, like HC-Pro itself, interferes with both the initiation and the maintenance of PTGS. This plant regulator of silencing is a novel calmodulin-related protein (thus "rgs-CaM") and studies of its function should provide important clues to elucidate other steps in the signaling pathway that regulates PTGS. The subject invention extends to the use of rgs-CaM polynucleotides and polypeptides as tools to manipulate the PTGS pathway for biotechnological applications.

It is an object of the present invention to provide methods for enhancing the expression of gene products in plants.

Another object of the present invention is to provide methods of enhancing the expression of introduced foreign and endogenous gene products in plants.

A further object of the present invention is to provide processes using polynucleotide booster sequences to enhance the expression of an introduced gene product in a plant.

Still another object of the present invention is to provide polynucleotides useful as probes for identifying homologs of rgs-CaM from other species.

Yet another object of the present invention is to provide a means to enhance gene silencing and thereby inhibit expression of genes which lead to undesirable traits.

These and other objects are achieved by providing a method for enhancing the expression of genes in plants by supplying a polynucleotide comprising a booster region comprising a booster sequence which encodes at least one polypeptide having rgs-CaM activity. Some portion of the booster sequence may be expressed either individually or fused to other sequences, a modified version of the booster sequence, a related sequence from another plant, or any portion or modified version of that related sequence sufficient to encode a polypeptide exhibiting rgs-CaM activity, expressed either individually or fused to another sequence. The booster sequence enhances the expression of foreign genes or endogenous plant genes that are introduced to the plant by employing any known methodology. One example of such known methods includes the expression of introduced genes from one or more copies of a gene stably incorporated into the plant genome. Another example of such known methods is the expression of genes introduced via plant viral expression vectors.

The process of enhancing gene expression may be carried out in various forms. For example, the booster sequence may be provided to the plant in a variety of ways. It may be provided by infection with a modified, transgenic virus that expresses the booster sequence as a viral gene product during its natural life cycle. Alternatively, the booster sequence may be introduced through use of a transgenic host plant expressing the booster sequence as an introduced gene. The booster sequence may also be introduced using the same viral expression vector utilized to express the introduced foreign or endogenous gene of interest. A transient expression system may be employed to temporarily express the booster sequence or a two-component co-infection system may be used wherein two viruses are required for successful boosting of gene expression. In the two-component co-infection system, one virus expresses the booster sequence while the other virus expresses the introduced gene of interest.

In addition, the booster sequence may be used to enhance expression of any introduced gene, including foreign genes or endogenous plant genes. The genes to be boosted may be introduced to the plant in a variety of ways. Foreign or endogenous genes may be introduced by means of stable transformation into the genome of the plant employing any of the known technologies used for this process. Alternatively, the foreign or endogenous gene may be introduced using any plant viral expression vector.

More specifically, the present invention involves a method of expressing a foreign gene or an endogenous plant gene that has been introduced into plant material, which includes plant cells, plant protoplasts, or whole plants, wherein the improvement comprises the supplying of a booster sequence comprising a polynucleotide which encodes at least one polypeptide having rgs-CaM activity to the plant material so that expression of said foreign gene or endogenous plant gene is enhanced. The plant gene may be a foreign gene not naturally occurring in the plant material prior to being introduced therein, or an endogenous plant gene that was naturally occurring in the plant material prior to being introduced as an additional copy or additional copies of the endogenous gene. The booster sequence supplied may comprise the coding region for rgs-CaM, and the booster sequence may be expressed independently or fused to other sequences.

The foreign or endogenous gene may be introduced to the plant via a viral expression vector with the booster sequence being supplied by expression from the same viral vector; introduced via a viral expression vector with the booster sequence being supplied by expression of one or more DNA copies of the booster sequence stably incorporated into the plant's genome; or introduced via a viral expression vector with the booster sequence being expressed from a transient expression system containing one or more DNA copies of said booster sequence. A two-component viral vector system may be utilized with one viral component expressing the booster sequence and the other viral component expressing the introduced gene. The introduced gene may be a foreign gene or endogenous plant gene introduced via a viral expression vector with the booster sequence being supplied by co-infection with a modified or transgenic virus that expresses the booster sequence, or introduced via a viral expression vector having the gene fused to the structural gene of interest of said viral expression vector.

In addition, the foreign gene or endogenous plant gene may be introduced into a plant genome via any mode of stable transformation of one or more DNA copies of the introduced gene, with the booster sequence being supplied prior to, during, or after introduction of the foreign gene or endogenous plant gene via stable transformation procedures so that it enhances either the expression of the introduced gene product or the number or proportion of transformant plants that express the introduced gene product. In this aspect, the booster sequence may be supplied via expression from one or more DNA copies of the booster sequence stably incorporated into the plant genome prior to, during, or after transformation of the plant material with said introduced gene product.

BRIEF DESCRIPTION OF THE SEQUENCES

Figure 1:
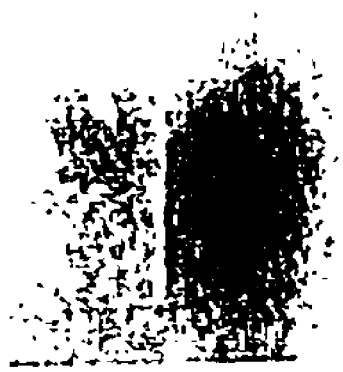
FIG. 1. Northern blot analysis showing that the rgs-CaM message is greatly overexpressed in the leaves of rgs-CaM transgenic lines (lane 2) compared to control non-transgenic plants (lane 1).

SEQ ID NO: 1 is the cDNA sequence for rgs-CaM.

SEQ ID NO: 2 is the amino acid sequence of the rgs-CaM polypeptide encoded by SEQ ID NO: 1.

DETAILED DISCLOSURE OF THE INVENTION

Post-transcriptional gene silencing (PTGS) is a fundamental regulatory mechanism operating in diverse types of organisms. Although PTGS was first identified in plant systems, similar pathways appear to operate in filamentous fungi, nematodes, and a variety of animal systems where it is referred to as RNA interference (Fire, 1999; Sharp, 1999; Grant, 1999; Sharp and Zamore, 2000). Double-stranded RNA (dsRNA) induces PTGS in many systems (Montgomery and Fire, 1998; Wianny and Zernicka-Goetz, 2000; Waterhouse and Graham, 1998) and, in plants, it can also be triggered by cytoplasmically replicating viruses, many of which produce dsRNA replication intermediates (Kumagai et al., 1995; Ratcliff et al., 1997). Once the mechanism is activated, any homologous RNA is degraded, whether it is transcribed from the transgene, the endogenous gene, or the viral RNA. The fact that plant viruses can act both as inducers and as targets of posttranscriptional gene silencing (Kumagai et al., 1995; Baulcombe, 1999) has led to the idea that PTGS evolved as a defense mechanism against viruses in plants. HC-Pro is a viral protein that has been shown to suppress PTGS. We have identified a number of proteins that interact with HC-Pro in the yeast two-hybrid system. One of these HC-Pro-interacting proteins, like HC-Pro itself, interferes with both the initiation and the maintenance of PTGS. The plant regulator of silencing is a novel calmodulin-related protein, termed rgs-CaM. Here we teach methods to exploit rgs-CaM as a tool for manipulating the PTGS pathway for biotechnological applications.

Manipulation of the PTGS pathway is an effective means for modulating expression of a gene of interest, or a "target sequence," in a plant. That is, the expression of the target sequence may be enhanced or, if desired, decreased or its silencing maintained. Generally, enhanced expression of the target sequence is effected. By "enhanced expression" is intended that expression of the target sequence is increased over expression observed in conventional transgenic lines for heterologous sequences and over endogenous levels of expression for homologous sequences, and particularly as compared to expression in systems of either type where the target sequence is subject to PTGS. An rgs-CaM polynucleotide which retains the ability to cause enhanced expression is sometimes referred to herein as a "booster sequence." Heterologous or exogenous sequences comprise sequences that do not occur in the plant of interest in its native state. Homologous or endogenous sequences are those that are natively present in the plant genome. Generally, expression of the target sequence is increased at least about 25%–50%, preferably about 50%–100%, more preferably about 100%–200% and greater. The methods of the invention provide for a substantial increase in expression, yet without apparent negative effects on the plant.

The invention relates to gene silencing, specifically the suppression of gene silencing in plants. However, in another aspect the invention relates to maintaining gene silencing in certain systems where desired. "Gene silencing" is generally used to refer to suppression of expression of a gene. The degree of reduction may be partial or total reduction in production of the encoded gene product. Therefore, the term should not be taken to require complete "silencing" of expression. Methods for gene silencing are known in the art and include co-suppression and antisense suppression. See, for example, PCT/GB98/00442 and PCT/GB98/02862, herein incorporated by reference.

The method of the invention relates to modulating the expression of a target gene or sequence in plants. The target sequence may be endogenous or exogenous in origin. For exogenous sequences, it is recognized that co-suppression or gene-silencing will generally require multiple copies of the exogenous sequence in the plant cell. Multiple copies may be obtained by multiple insertion events from the same transformation event, subsequent transformation of a plant having the exogenous sequence incorporated in the plant genome, genetic crossing, and the like. Additionally, an exogenous sequence may be contained as part of a viral replicon or plant viral expression vector.

The target sequence comprises any sequence of interest, including genes, regulatory sequences, etc. Genes of interest include those encoding agronomic traits, insect resistance, disease resistance, herbicide resistance, sterility, grain characteristics, and the like. The genes may be involved in metabolism of oil, starch, carbohydrates, nutrients, etc. Genes or traits of interest include, but are not limited to, environmental- or stress-related traits, disease-related traits, and traits affecting agronomic performance. Target sequences also include genes responsible for the synthesis of proteins, peptides, fatty acids, lipids, waxes, oils, starches, sugars, carbohydrates, flavors, odors, toxins, carotenoids, hormones, polymers, flavonoids, storage proteins, phenolic acids, alkaloids, lignins, tannins, celluloses, glycoproteins, glycolipids, etc.

Variants or sequences having substantial identity or homology with the enhancer molecules may be utilized in the practice of the invention. That is, the booster sequence may be modified yet still retain the ability to act as a suppressor of post-transcriptional gene silencing. Generally, the booster will comprise at least about 40%–60%, preferably about 60%–80%, more preferably about 80%–90%, and even more preferably about 90%–95% sequence identity with the native booster sequence.

Sequence relationships between two or more nucleic acids or polynucleotides are generally defined as sequence identity, percentage of sequence identity, and substantial identity. In determining sequence identity, a "reference sequence" is used as a basis for sequence comparison. The reference may be a subset or the entirety of a specified sequence. That is, the reference sequence may be a full-length gene sequence or a segment of the gene sequence.

Methods for alignment of sequences for comparison are well known in the art. See, for example, Smith et al. (1981) *Adv. Appl. Math.* 2:482; Needleman et al. (1970) *J. Mol. Biol.* 48:443; Pearson et al. (1988) *Proc. Natl. Acad. Sci.* 85:2444; CLUSTAL in the PC/Gene Program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis. USA. Preferred computer alignment methods also include the BLASTP, BLASTN, and BLASTX algorithms. See, Altschul et al. (1990) *J. Mol. Biol.* 215:403–410.

"Sequence identity" or "identity" in the context of nucleic acid or polypeptide sequences refers to the nucleic acid bases or residues in the two sequences that are the same when aligned for maximum correspondence over a specified comparison window. "Percentage of sequence identity" refers to the value determined by comparing two optimally aligned sequences over a comparison window, wherein the portion of the polynucleotide sequence in the comparison window may comprise additions or deletions as compared to the reference window for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Polynucleotide sequences having "substantial identity" are those sequences having at least about 50%–60% sequence identity, generally at least 70% sequence identity, preferably at least 80%, more preferably at least 90%, and most preferably at least 95%, compared to a reference sequence using one of the alignment programs described above. Preferably sequence identity is determined using the default parameters determined by the program. Substantial identity of amino acid sequence generally means sequence identity of at least 50%, more preferably at least 70%, 80%, 90%, and most preferably at least 95%.

Nucleotide sequences are generally substantially identical if the two molecules hybridize to each other under stringent conditions. Generally, stringent conditions are selected to be about 5° C. lower than the thermal melting point for the specific sequence at a defined ionic strength and pH. Nucleic acid molecules that do not hybridize to each other under stringent conditions may still be substantially identical if the polypeptides they encode are substantially identical. This may occur, for example, when a copy of a nucleic acid is created using the maximum codon degeneracy permitted by the genetic code.

As noted, hybridization of sequences may be carried out under stringent conditions. By "stringent conditions" is intended conditions under which a probe will hybridize to its target sequence to a detectably greater degree than to other sequences. Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary stringent conditions include hybridization with a buffer solution of 30 to 35% formamide, 1.0 M NaCl, 1% SDS (sodium dodecyl sulphate) at 37° C., and a wash in 1× to 2×SSC (20×SSC=3.0 M NaCl/0.3 M trisodium citrate) at 50 to 55° C. It is recognized that the temperature, salt, and wash conditions may be altered to increase or decrease stringency conditions. For the post-hybridization washes, the critical factors are the ionic strength and temperature of the final wash solution. See, Meinkoth and Wahl (1984) *Anal. Biochem.* 138:267–284.

As indicated, fragments and variants of the nucleotide sequences of the invention are encompassed herein. By "fragment" is intended a portion of the nucleotide sequence. Fragments may be generated by a number of methods well known in the art, such as by use of commercially available restriction enzymes, exonucleases such as Bal31, or by chemical synthesis. Fragments of the booster sequence will generally encode polypeptides which retain one or more of the biological activities of the native protein. Activities can be tested and confirmed by following examples set forth herein. Alternatively, fragments of the polynucleotide sequences may or may not retain biological activity. Such sequences may be useful as hybridization probes, as antisense constructs, or as co-suppression sequences. Thus, fragments of a nucleotide sequence may range from at least about 15–20 nucleotides, about 50 nucleotides, about 100 nucleotides, and up to the full-length nucleotide sequence of the particular polynucleotide of interest.

By "variants" is intended substantially similar sequences. For example, for nucleotide sequences, conservative variants include those sequences that, because of the degeneracy of the genetic code, encode the amino acid sequence of the booster of the invention. Variant nucleotide sequences include synthetically derived sequences, such as those generated for example, using site-directed mutagenesis. Generally, nucleotide sequence variants of the invention will have at least 40%, 50%, 60%, 70%, generally 80%, preferably 85%, 90%, and up to 95% or more sequence identity to its respective native nucleotide sequence. Thus, some fragments may also be variants.

"Variant" in the context of proteins is intended to mean a protein derived from the native protein by deletion or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or human manipulation. Conservative amino acid substitutions will generally result in variants that retain biological function. Variant proteins that retain a desired biological activity are encompassed within the subject invention. Variant proteins of the invention may include those that are altered in various ways including amino acid substitutions, deletions, truncations, and insertions. Methods for such manipulation are generally known in the art. See, for example, Kunkel (1985) *Proc. Natl. Acad. Sci. USA* 82:488–492; Kunkel et al. (1987) *Methods and Enzymol;* 154:367–382; and the references cited therein.

The methods of the invention are useful in any situation where increased expression of a nucleotide sequence is desired. Thus, the methods are useful for increasing the expression of endogenous as well as exogenous sequences. For example, for exogenous sequences, the booster sequence can be used to enhance expression of transgene-induced gene silencing. Therefore, the target sequence may be any nucleotide sequence of interest. In one embodiment, the methods can be used to produce peptides or proteins that cannot effectively be commercially produced by existing gene expression systems. For example, some proteins cannot be expressed in mammalian systems because the protein interferes with cell viability, cell proliferation, cellular differentiation, or protein assembly in mammalian cells. Such proteins include, but are not limited to, retinoblastoma protein, p53, angiostatin, and leptin. Likewise, the methods of the invention can be used to produce mammalian regulatory proteins. Other sequences of interest include proteins, hormones, growth factors, cytokines, preferably insulin, growth hormone, particularly human growth hormone, interferon, particularly α-interferon, β-glucocerebrosidase, serum albumin, particularly human serum albumin, hemoglobin, collagen, etc. In such instances, generally, the booster sequence will be operably linked to a constitutive promoter.

In other instances, inducible promoters may be utilized. In one embodiment, the methods may be used to express disease and insect resistance genes in the plant. In this manner, enhancer sequences may be operably linked to a pathogen inducible promoter for enhanced disease resistance in a plant. It is recognized that some plant resistance is based on post-transcriptional gene silencing and such mechanisms may not work in the present invention. However, resistance mechanisms based on proteins would benefit the plant.

Insect resistance may be enhanced by expression of the booster sequence with a wound-inducible promoter such that the resistance genes, such as *Bacillus* toxins, would be expressed at the site of the insect invasion. It is recognized that the pathogen resistance and insect resistance target sequences may be expressed by constitutive promoters. However, the use of an inducible promoter driving the booster sequence may benefit the plant from a yield and growth standpoint.

In another embodiment, the methods of the invention can be used to produce transgenic seed and seed products. In this manner, target sequences or genes of interest or, alternatively, the booster sequence can be operably linked with a seed-preferred, or endosperm promoter. Such seed proteins of interest include, but are not limited to, starches, storage proteins, proteins with enhanced nutritional value, specialty oils, carotenoids, etc.

Generally, the methods of the invention can be used for the increased expression of any target gene or sequence of interest, including therapeutic or immunogenic peptides and proteins, nucleic acids for controlling gene expression, genes to reproduce enzymatic pathways for chemical synthesis, genes to shunt an enzymatic pathway for enhanced expression of a particular intermediate or final product, industrial processes, and the like.

It is recognized that the methods of the invention can be used for enhanced expression in transformed plants, plant cells and tissues, seed, and the like. Thus, in some embodiments, it may be beneficial to provide the methods in a plant culture system for production of peptides or proteins of interest.

As discussed, a number of promoters can be used in the practice of the invention. The promoters can be selected based on the desired outcome. Generally, the booster sequence can be combined with promoters of choice to create increased expression of the target sequences in the tissue or organ of choice. However, in some instances, the targeting sequence may comprise a tissue, developmental, or inducible promoter for co-suppression and subsequent increased expression of the target sequence in particular tissues, organs, or developmental stages of the plant. Thus, the booster sequences can be combined with constitutive, tissue-specific, inducible, developmental, or other promoters for expression in plants depending upon the desired outcome.

Constitutive promoters include, for example, CaMV 35S promoter (Odell et al. (1985) *Nature* 313:810–812; rice actin (McElroy et al. (1990) *Plant Cell* 2:163–171; ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680; 5,268,463; and 5,608,142.

A number of inducible promoters are known in the art. For resistance genes, a pathogen-inducible promoter can be utilized. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. Of particular interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386; Cordero et al. (1992) *Physiol. Mol. Plant Path.* 41:189–200; and the references cited therein.

Additionally, as pathogens find entry into plants through wounds or insect damage, a wound-inducible promoter may be used in the DNA constructs of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498; wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150; and the like. Such references are herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression; or a chemical-repressible promoter, where application of the chemical represses gene expression. Chemical-inducible promoters are known in the art and include, but are not limited to, the maize In2-2 promoter, which is activated by benzenesulfonamide herbicide safeners; the maize GST promoter, which is activated by hydrophobic electrophilic compounds that are used as preemergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci USA* 88:10421–10425 and McNellis et al. (1998) *Plant J.* 14(2):247–257), and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Where enhanced expression in particular tissues is desired, tissue-specific promoters can be utilized. Tissue-specific promoters include those taught in Yamamoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343; Russel et al. (1997) *Transgenic Res.* 6(2):157–168; Rinehart et al. (1996) *Plant Physiol.* 112(3): 1331–1341; Van Camp et al. (1996) *Plant Physiol.* 112(2): 525–535; Canevasini et al. (1996) *Plant Physiol.* 112(2): 513–524; Yamamoto et al. (1994) *Plant Cell Physiol.* 35(5): 773–778; Lam (1994) *Results Probl. Cell Differ.* 20:181–196; Orozco et al. (1993) *Plant Mol. Biol.* 23(6): 1129–1138; Matsuoka et al. (1993) *Proc Natl. Acad. Sci. USA* 90(20):9586–9590; and Guevara-Garcia et al. (1993) *Plant J.* 4(3):495–505.

Leaf-specific promoters can similarly be used if desired, an are taught in references which include Yamamoto et al. (1997) *Plant J.* 12(2):255–265; Kawamata et al. (1997) *Plant Cell Physiol.* 38(7):792–803; Hansen et al. (1997) *Mol. Gen. Genet.* 254(3):337–343; Russel et al. (1997)

Transgenic Res. 6(2):157–168; Rinehart et al. (1996) Plant Physiol. 112(3):1331–1341; Van Camp et al. (1996) Plant Physiol. 112(2):525–535; Canevascini et al. (1996) Plant Physiol. 112(2):513–524; Yamamoto et al. (1994) Plant Cell Physiol. 35(5)773–778; Lam (1994) Results Probl. Cell Differ. 20:181–196; Orozco et al. (1993) Plant Mol. Biol. 23(6):1129–1138; Matsuoka et al. (1993) Proc. Natl. Acad. Sci USA:90(20) 9586–9590; and Guevara-Garcia et al. (1993) Plant J. 4(3):495–505.

Root-specific promoters are known and can be selected from the many available from the literature. See, for example, Hire et al. (1992) Plant Mol. Biol. 20(2):207–218 (soybean root-specific glutamine synthetase gene); Keller and Baumgartner (1991) Plant Cell 3(10):1051–1061 (root-specific control element in the GRP 1.8 gene of French bean); Sanger et al. (1990) Plant Mol. Biol. 14(3):433–443 (root-specific promoter of the mannopine synthase (MAS) gene of Agrobacterium tumefaciens) Miao et al. (1991) Plant Cell 3(1):11–22 (full-length cDNA clone encoding cytosolic glutamine synthetase (GS), which is expressed in roots and root nodules of soybean). Bogusz et al. (1990) Plant Cell 2(7):633–641 (root specific promoters from hemoglobin genes from the nitrogen-fixing nonlegume Parasponia andersonii and the related non-nitrogen-fixing nonlegume Trema tomeniosa; Leach and Aoyagi (1991) Plant Science (Limerick) 79(1):69–76 (rolC and rolD root-including genes of Agrobacterium rhizogenes); Teeri et al. (1989) EMBO J. 8(2):343–350 (octopine synthase and TR2' gene); (VfENOD-GRP3 gene promoter); Kuster et al. (1995) Plant Mol. Biol. 29(4):759–772 and Capana et al. (1994) Plant Mol. Biol. 25(4):681–691 (rolB promoter). See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) Bioassays 10:108, herein incorporated by reference. Such seed-preferred promoters include, but are not limited to, Cim1 (cytokinin-induced message); cZ10B1 (Maize 19 kDa zein); ce1A (cellulose synthase); gama-zein; Glob-1; bean β-phaseolin; napin; β-conglycinin; soybean lectin; cruciferin; maize 15 kDa zein; 22 kDa zein; 27 kDa zein; g-zein; waxy; shrunken 1; shrunken 2; globulin 1; etc.

The booster sequences of the invention may be provided in DNA constructs or expression cassettes for expression in the plant of interest. The cassette will include 5' and 3' regulatory sequences operably linked to a booster sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

The expression cassette may additionally contain at least one additional gene to be cotransformed into the organism. Alternatively, the additional gene(s) can be provided on multiple expression cassettes.

Such an expression cassette is provided with a plurality of restriction sites for insertion of the sequences of the invention to be under the transcriptional regulation of the regulatory regions. The expression cassette may additionally contain selectable marker genes.

The expression cassette will include in the 5'-3' direction of transcription, a transcriptional and translational initiation region, a DNA sequence of the invention, and a transcriptional and translational termination region functional in plants. The transcriptional initiation region, the promoter, may be native or analogous, or foreign or heterologous, to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcriptional initiation region that is heterologous to the coding sequence.

The termination region may be native with the transcriptional initiation region, may be native with the operably linked DNA sequence of interest, or may be derived from another source. Convenient termination regions are available from the Ti-plasmid of A. tumefaciens, such as the octopine synthase and nopaline synthase termination regions. See also Guerineau et al. (1991) Mol. Gen. Genet. 262:141–144; Proudfoot (1991) Cell 64:671–674; Sanfacon et al. (1991) Genes Dev. 5:141–149; Mogen et al. (1990) Plant Cell 2:1261–1272; Munroe et al. (1990) Gene 91:151–158; Ballas et al. (1989) Nucleic Acids Res. 17:7891–7903; and Joshi et al. (1987) Nucleic Acid Res. 15:9627–9639.

Where appropriate, the gene(s) for which expression is to be enhanced may be optimized for expression in the transformed plant. That is, the genes can be synthesized using plant-preferred codons corresponding to the plant of interest. Methods are available in the art for synthesizing plant-preferred genes. See, for example, U.S. Pat. Nos. 5,380,831 and 5,436,391, and Murray et al. (1989) Nucleic Acids Res. 17:477–498, herein incorporated by reference.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region), Elroy-Stein et al. (1989) PNAS USA 86:6126–6130; potyvirus leaders, for example, TEV leader (Tobacco Etch Virus), Allison et al. (1986); MDMV Leader (Maize Dwarf Mosaic Virus), Virology 154:9–20; human immunoglobulin heavy-chain binding protein (BiP), Macejak et al. (1991) Nature 353:90–94; untranslated leader from the coat protein mRNA of alfalfa mosaic virus (AMV RNA 4), Jobling et al. (1987) Nature 325:622–625; tobacco mosaic virus leader (TMV), Gallie et al. (1989) in Molecular Biology of RNA, ed. Cech (Liss, New York), pp. 237–256; and maize chlorotic mottle virus leader (MCMV), Lommel et al. (1991) Virology 81:382–385. See also, Della-Cioppa et al. (1987) Plant Physiol. 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Plants transformed with a DNA construct of the invention may be produced by standard techniques known in the art for the genetic manipulation of plants. DNA can be transformed into plant cells using any suitable technology, such as a disarmed Ti-plasmid vector carried by *Agrobacterium* exploiting its natural gene transferability (EP-A-270355; EP-A-0116718; *NAR* 12(22):87211–87215 (1984); Townsend et al., U.S. Pat. No. 5,563,055); particle or microprojectile bombardment (U.S. Pat. No. 5,100,792; EP-A-444882; EP-A-434616; Sanford et al. U.S. Pat. No. 4,945,050; Tomes et al. (1995) "*Direct DNA Transfer Into Plant Cells via Microprojectile Bombardment*," in *Plant Cell, Tissue, and Organ Culture: Fundamental Methods*, ed. Gamborg and Phillips (Springer-Verlag, Berlin); and McCabe et al. (1988) *Biotechnology* 6:923–926); microinjection (WO 92/09696; WO 94/00583; EP 331083; EP 175966; Green et al. (1987) *Plant Tissue and Cell Culture*, Academic Press; Crossway et al. (1986) *Biotechniques* 4:320–334); electroporation (EP 290395; WO 8706614; Riggs et al. (1986) *Proc. Nat. Acad. Sci. USA* 83:5602–5606; D'Halluin (1992) *Plant Cell* 4:1495–1505); other forms of direct DNA uptake (DE 4005152; WO 9012096; U.S. Pat. No. 4,684,611; Paszkowski et al. (1984) *EMBO J.* 3:2717–2722); liposome-mediated DNA uptake (e.g., Freeman et al. (1984) *Plant Cell Physiol.* 29:1353); or the vortexing method (e.g., Kindle (1990) *Proc. Nat. Acad. Sci. USA* 87:1228). Physical methods for the transformation of plant cells are reviewed in Oard (1991) *Biotech. Adv.* 9:1–11. See generally, Weissinger et al. (1988) *Ann. Rev. Genet.* 22:421–477; Sanford et al. (1987) *Particulate Science and Technology* 5:27–37; Christou et al. (1988) *Plant Physiol.* 87:671–674; McCabe et al. (1988) *Bio/Technology* 6:923–926; Finer and McMullen (1991) *In Vitro Cell Dev. Biol.* 27P:175–182; Singh et al. (1998) *Theor. Appl. Genet.* 96:319324; Datta et al. (1990) *Biotechnology* 8:736–740; Klein et al. (1988) *Pro. Natl. Acad. Sci. USA* 85:4305–4309; Klein et al. (1988) *Biotechnology* 6:559–563; Tomes, U.S. Pat. No. 5,240,855; Buising et al., U.S. Pat. Nos. 5,322,783 and 5,324,646; Klein et al. (1988) *Plant Physiol.* 91:440–444; Fromm et al. (1990) *Biotechnology* 8:833–839; Hooykaas-Van Slogteren et al. (1984) *Nature* (London) 311:763–764; Bytebier et al. (1987) *Proc. Natl. Acad. Sci. USA* 84:5345–5349; De Wet et al. (1985) in *The Experimental Manipulation of Ovule Tissues*, ed. Chapman et al. (Longman, New York), pp. 197–209; Kaeppler et al. (1990) *Plant Cell Reports* 9:415–418 and Kaeppler et al. (1992) *Theor. Appl. Genet.* 84:560–566; Li et al. (1993) *Plant Cell Reports* 12:250–255; Christou and Ford (1995) *Annals of Botany* 75:407–413; and Osjoda et al. (1996) *Nature Biotechnology* 14:745–750; all of which are herein incorporated by reference.

*Agrobacterium* transformation is widely used by those skilled in the art to transform dicotyledonous species. Recently, there has been substantial progress towards the routine production of stable, fertile transgenic plants in almost all economically relevant monocot plants (Toriyama et al. (1988) *Bio/Technology* 6:1072–1074; Zhang, et al. (1988) *Plant Cell Rep.* 7:379–384; Zhang et al. (1988) *Theor. Appl. Genet.* 76:835–840; Shimamoto et al. (1989) *Nature* 338:274–276; Datta et al. (1990) *Bio/Technology* 8:736–740; Christou et al. (1991) *Biotechnology* 9:957–962; Peng et al. (1991) International Rice Research Institute, Manila, Philippines, pp. 563–574; Cao et al. (1992) *Plant Cell Rep.* 11:585–591; Li et al. (1993) *Plant Cell Rep.* 12:250–255; Rathore et al. (1993) *Plant Mol. Biol.* 21:871–884; Fromm et al. (1990) *Bio/Technology* 8:833–839; Gordon-Kamm et al. (1990) *Plant Cell* 2:603–618; D'Halluin et al. (1992) *Plant Cell* 4:1495–1505; Walters et al. (1992) *Plant Mol. Biol.* 18:189–200; Koziel et al. (1993) *Biotechnology* 11:194–200; Vasil, I. K. (1994) *Plant Mol. Biol.* 25:925–937; Weeks et al. (1993) *Plant Physiol.* 102:1077–1084; Somers et al. (1992) *Bio/Technology* 10:1589–1594; WO 92/14828). In particular, *Agrobacterium* mediated transformation is now emerging also as a highly efficient transformation method in monocots (Hiei, et al. (1994) *The Plant Journal* 6:271–282). See also, Shimamoto, K. (1994) *Current Opinion in Biotechnology* 5:158–162; Vasil, et al. (1992) *Bio/Technology* 10:667–674; Vain, et al. (1995) *Biotechnology Advances* 13(4):653–671; Vasil et al. (1996) *Nature Biotechnology* 14:702.

Microprojectile bombardment, electroporation, and direct DNA uptake are preferred where *Agrobacterium* is inefficient or ineffective. Alternatively, a combination of different techniques may be employed to enhance the efficiency of the transformation process, e.g., bombardment with *Agrobacterium*-coated microparticles (EP-A-486234) or microprojectile bombardment to induce wounding followed by co-cultivation with *Agrobacterium* (EP-A-486233).

Following transformation, a plant may be regenerated, e.g., from single cells, callus tissue or leaf discs, as is standard in the art. Almost any plant can be entirely regenerated from cells, tissues, and organs of the plant. Available techniques are reviewed in Vasil et al. (1984) in *Cell Culture and Somatic Cell Genetics of Plants, Vols. I, II, and III, Laboratory Procedures and Their Applications* (Academic press); and Weissbach et al. (1989) *Methods for Plant Mol. Biol.*

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited, and then seeds harvested to ensure expression of the desired phenotypic characteristic has been achieved.

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

Also according to the invention, there is provided a plant cell having the constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

The present invention also provides a plant comprising a plant cell as disclosed. Transformed seeds and plant parts are also encompassed.

In addition to a plant, the present invention provides any clone of such a plant, seed, selfed or hybrid descendants, and any part of any of these, such as cuttings or seed. The invention provides any plant propagule, that is any part which may be used in reproduction or propagation, sexual or asexual, including cuttings, seed, and so on. Also encompassed by the invention is a plant which is a sexually or asexually propagated off-spring, clone, or descendant of such a plant; or any part or propagule of said plant, offspring, clone, or descendant. Plant extracts and derivatives are also provided.

The present invention may be used for transformation of any plant species, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* ssp.), coconut (*Cocos nucifera*), pineapple (*Ananas comosus*), citrus trees (*Citrus* ssp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidental*), macadamia (*Macadamia integrifolia*), almond (*Prunus anygdalus*), sugar beets (*Beta vulgaris*), oats, barley, vegetables, ornamentals, and conifers.

Preferably, plants of the present invention are crop plants (for example, cereals and pulses, maize, wheat, potatoes, tapioca, rice, sorghum, millet, cassava, barley, pea, and other root, tuber, or seed crops. Important seed crops are oil-seed rape, sugar beet, maize, sunflower, soybean, and sorghum. Horticultural plants to which the present invention may be applied may include lettuce; endive; and vegetable brassicas including cabbage, broccoli, and cauliflower; and carnations and geraniums. The present invention may be applied to tobacco, cucurbits, carrot, strawberry, sunflower, tomato, pepper, chrysanthemum, poplar, eucalyptus, and pine.

Grain plants that provide seeds of interest include oil-seed plants and leguminous plants. Seeds of interest include grain seeds, such as corn, wheat, barley, rice, sorghum, rye, etc. Oil seed plants include cotton, soybean, safflower, sunflower, Brassica, maize, alfalfa, palm, coconut, etc. Leguminous plants include beans and peas. Beans including guar, locust bean, fenugreek, soybean, garden beans, cowpea, mungbean, lima bean, fava bean, lentils, chickpea, etc.

Since the effect of HC-Pro on suppression of PTGS is clearly protein-mediated rather than RNA-mediated (Anandalakshmi et al., 1998; Brigneti et al., 1998), we used protein-protein interaction assays to search for plant proteins that interact with HC-Pro. Using HC-Pro as bait in a yeast two-hybrid system, we found four HC-Pro-interacting plant proteins. Our overall approach has been to overexpress or interfere with the expression of these proteins and then assay the effect of the manipulations on gene silencing and its modulation by HC-Pro. These methods have already successfully identified one of the HC-Pro-interactors as a plant regulator of silencing. The plant regulator of silencing is a novel calmodulin-related protein (rgs-CaM). This cellular protein, like HC-Pro itself (Brigneti et al., 1998), reverses PTGS when expressed from a viral vector and interferes with the initiation of virus-induced gene silencing when expressed ectopically in transgenic plants.

The silencing suppressor activity of HC-Pro can be separated from its detrimental developmental phenotype. Two observations indicate that this is the case. Several transgenic tobacco lines that express mutant versions of P1/HC-Pro are available. One of these mutant lines does not have the usual "HC-Pro" developmental phenotype. It looks completely normal and grows at a normal rate. When crossed with a GUS-silenced line, it was noted that the mutant P1/HC-Pro failed to lift GUS silencing in the vascular tissue of the offspring, but did so in all other tissues of the plant Thus, tissue specific expression of HC-Pro or rgs-CaM can yield plants that suppress PTGS but are phenotypically normal.

The role of rgs-CaM in regulating PTGS allows manipulation of this pathway, which can be exploited in two different ways. 1) Suppression of the pathway (for example by over expression of rgs-CaM) allows stable high level expression of beneficial transgenes in plants. 2) In some cases, PTGS is used to eliminate the expression of detrimental or unwanted genes. In those cases, it is possible to use rgs-CaM to enhance PTGS and thus stabilize the silenced phenotype desired in these applications. HC-Pro is a multifunctional protein impacting pathways that affect both developmental and defense pathways in plants. Since the effects of HC-Pro on plant defense and development are mediated by interactions with cellular proteins that normally regulate these processes, it is possible to use the HC-Pro-interacting proteins such as rgs-CaM to engineer plants to express only one aspect of the "HC-Pro" phenotype.

By cloning mutant versions of rgs-CaM into a PVX vector and assaying the ability of the construct to reverse PTGS, one can assay the activity of rgs-CaM variants. This reversal of gene silencing assay is currently in use in the lab and was used to demonstrate that rgs-CaM is a regulator of PTGS Following are examples which illustrate procedures for practicing the invention. These examples should not be construed as limiting. All percentages are by weight and all solvent mixture proportions are by volume unless otherwise noted.

EXAMPLE 1

Isolation of cDNAs Encoding HC-Pro Interacting Proteins from Tobacco

In order to identify HC-Pro-interacting plant proteins, we screened a yeast two-hybrid tobacco cDNA library (kindly provided by Dr. Chris Mau, UG Davis) using the tobacco etch viral HC-Pro as bait. Two million cDNAs were screened and sixteen HC-Pro-interacting tobacco cDNAs were isolated on the basis of ability to grow in the absence of histidine and to activate the lacZ gene. Eight of these tobacco cDNAs met the following criteria. They did not interact with empty bait or negative control (lamin) plasmids and, when cloned into the DNA binding domain fusion plasmid, they interacted positively with HC-Pro in the activation domain fusion plasmid (reciprocal positives). The cDNAs for these eight putative HC-Pro interacting proteins were sequenced and comparative sequences analyses were carried out using the programs BLAST and FASTA. The cDNA encoding rgs-CaM was identified [SEQ ID NO: 1]. Based on this sequence, rgs-CaM homologues from other species have been identified and can be used according to the teachings herein, including tomato [GENBANK accession #AI487362], soybean [GENBANK accession #AW350323], and *Arabidopsis* [GENBANK accession #AB016888, translation of nucleotides 22076 through 21546].

HC-Pro-interacting protein B-3 (rgs-CaM) [SEQ ID NO: 2] shows high homology to calmodulins and related calcium binding proteins at its C-terminus, but with a 50 amino acid extension at its N-terminus. Subsequent experiments with B-3 led to the discovery that it acts as a regulator of gene silencing and these results are discussed in more detail in the following examples. Since the B-3 protein is a novel calmodulin-related protein and it regulated gene silencing, we named it rgs-CaM, for regulator of gene silencing (rgs), calmodulin-related protein (CaM).

Calmodulin (CaM) is a major intracellular receptor for the second messenger $Ca^{2+}$ and is expressed in every cell of all eukaryotes (Rudd and Franklin-Tong, 1999; Snedden and Hillel, 1999). It is a signaling molecule which has no enzymatic activity of its own, but binds to $Ca^{2+}$ and changes conformation allowing it to bind to specific target proteins and alter their activity. In general, CaM binds to and masks an autoinhibitory domain on the target protein and thereby activates it. All plants appear to have calmodulins that resemble the mammalian calmodulin. However, recent studies have identified a family of calmodulin-related proteins in plants distinct from the generic calmodulin in mammals. All these CaM and CaM-like molecules contain a common structural motif called the "EF hand", a helix-loop-helix structure that binds to a single $Ca^{2+}$ ion. Mammalian CaM has four EF hands, while CaM-related proteins of plants have varying numbers of this motif ranging from three to six, and many have either C- or N-terminal extensions as compared to CaM. Plant CaM-related proteins appear to differ in their ability to activate known CaM targets, and it is thought that there might be target specificity for different members of the plant CaM superfamily. Full-length native rgs-CaM has three EF hands and an N-terminal extension of about 40–50 amino acids that may specify the intracellular location or regulatory properties of rgs-CaM. The following examples disclose a variety of biochemical and genetic approaches to demonstrate the activity of the protein and how it transduces a signal that affects gene silencing.

EXAMPLE 2

Stable Transformation Experiments Using the rgs-CaM cDNAs

To demonstrate the role of rgs-CaM we overexpress or interfere with the expression of rgs-CaM cDNAs using stable transformation techniques. An alternative approach using potato virus X (PVX) as a vector to express high levels of rgs-CaM was pursued simultaneously.

Initial stable transformation experiments use cDNAs for rgs-CaM under control of the strong cauliflower mosaic virus 35S promoter for stable transformation of both *Nicotiana tabacum* (tobacco) and *N. benthamiana* (a species related to tobacco that is well suited for experiments using viral vectors). Greater than 30 individual primary transformants in both tobacco species are obtained. The primary transformants are selfed and are analyzed for segregation of the transgene (initially inferred by selection on kanamycin). Lines that segregate 3:1 for kanamycin resistance and also have a visible phenotype are selected for further studies. The selected lines are analyzed by Southern blot analysis to determine the number of transgenes, by Northern blot analysis to determine the level of expression of the transgene (and thus determine if the transgene is overexpressed or silenced) and for changes in gene silencing characteristics using a number of assays.

Interestingly, rgs-CaM cDNAs confer a characteristic phenotype in a number of the *N. benthamiana* primary transformants. The phenotypes of these transgenic lines might be conferred either by increased expression or by reduced expression of the particular transgene. Reduced expression of a transgene generally occurs in some fraction of transgenic lines due to either transcriptional or post-transcriptional gene silencing. The phenotype of rgs-CaM primary transformants in *N. benthamiana* is particularly interesting because it mimics that of plants transformed with HC-Pro. These rgs-CaM transgenic plants are found to greatly overexpress rgs-CaM in RNA as compared to non-transgenic controls. See FIG. 1, lanes 1 and 2. This indicates that rgs-CaM is a plant suppressor of PTGS.

EXAMPLE 3 rgs-CaM is a Plant Regulator of Post-Transcriptional Gene Silencing

Figure 2:
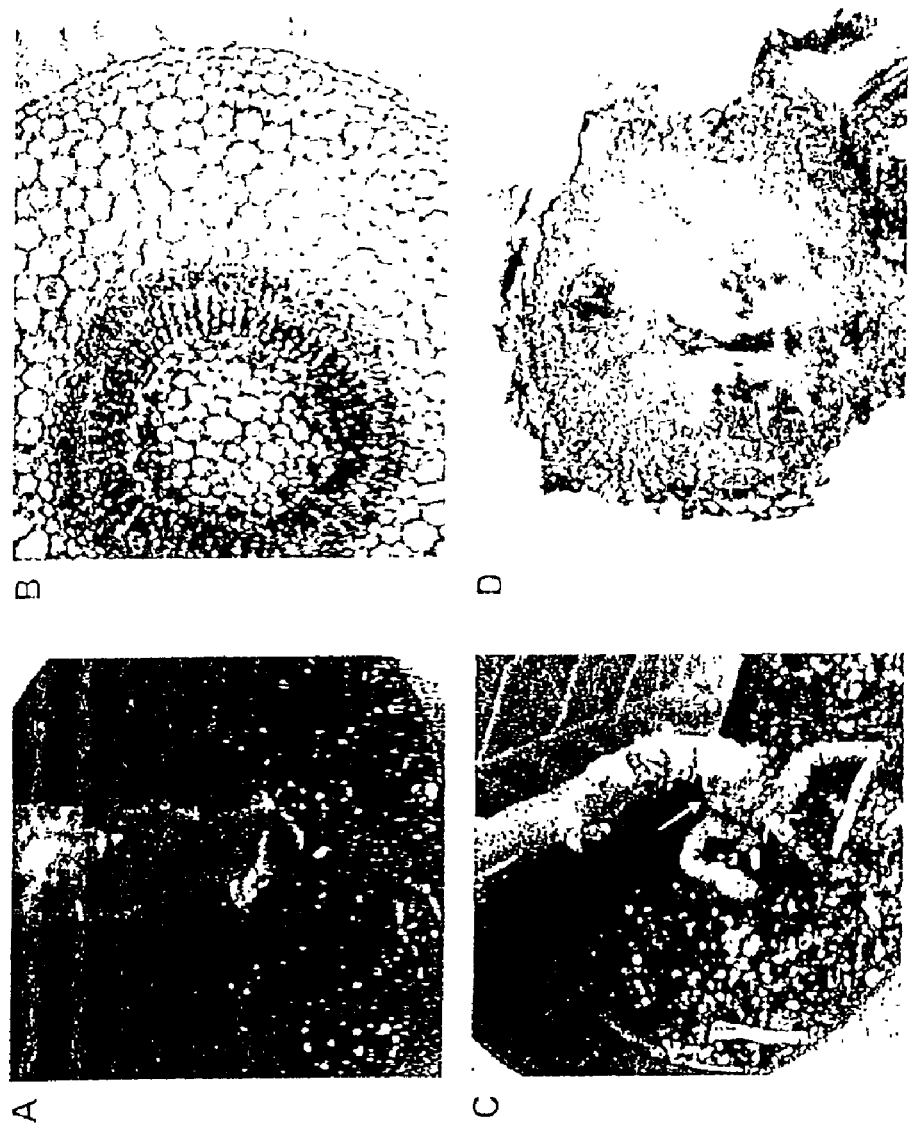
FIG. 2. Stem-root junctions showing tumor in P1/HC-Pro transgenic line. (A) Normal tobacco control; (B) cross-sectional view showing cellular organization in normal control; (C) P1/HC-Pro transgenic tobacco; (D) cross-sectional view, showing aberrant organization in tumor.

The phenotype of a number of independent rgs-CaM expressing transgenic lines is found to mimic that seen in P1/HC-Pro transgenic lines, and this surprising finding indicates that rgs-CaM, like P1/HC-Pro, acts as a regulator of silencing. We use two different assays to directly demonstrate the ability of this protein to affect gene silencing. There are four lines of evidence that rgs-CaM regulates PTGS and these are described below:

1) The phenotype of rgs-CaM transgenic lines mimics that of transgenic plants expressing the HC-Pro suppressor of silencing. Expression of P1/HC-Pro in transgenic plants confers several unique developmental characteristics, the most prominent of which are slow growth with reduced root biomass and development of a tumor at the junction of the stem and the root (compare the tumor in FIG. 2C to normal stem/root junction in FIG. 2A). The tumor associated with expression of P1/HC-Pro has a differentiated cytology (i.e. all the appropriate differentiated cell types are present, but the cell types are improperly arranged) (compare the aberrant organization of cells in FIG. 2D to the normal organization shown in FIG. 2B).

Figure 3:
FIG. 3. Stem-root junctions showing tumor in rgs-CaM transgenic line. (A) normal *N. benthamiana* control; (B) tumor in rgs-CaM transgenic *N. benthamiana*.

Several of the *N. benthamiana* rgs-CaM primary transformants develop a phenotype reminiscent of that seen in *N. tabacum* plants expressing the potyviral P1/HC-Pro suppressor of gene silencing. They grow slowly and have a tumorous growth which develops at the junction of the stem and the root (FIG. 3). Like the HC-Pro transgenic lines, these rgs-CaM tumors are composed of differentiated cells that are aberrantly arranged (data not shown). These results suggest that post-transcriptional gene silencing is used during normal plant development and that suppression of this mechanism produces developmental anomalies. The fact that rgs-CaM transgenic lines have a phenotype similar to that seen in transgenics expressing the viral suppressor indicates that rgs-CaM is a cellular regulator of PTGS and that this protein acts, at least in part, to mediate the suppressor activity of HC-Pro.

Figure 4:
FIG. 4. rgs-CaM transgenic line is deficient in VIGS. (A) GFP transgene is silenced in GFP-transgenic line when infected with PVX-GFP; (B) GFP transgene is not silenced in lines transgenic for both GFP and rgs-CaM when infected with PVX-GFP.
Figure 4:
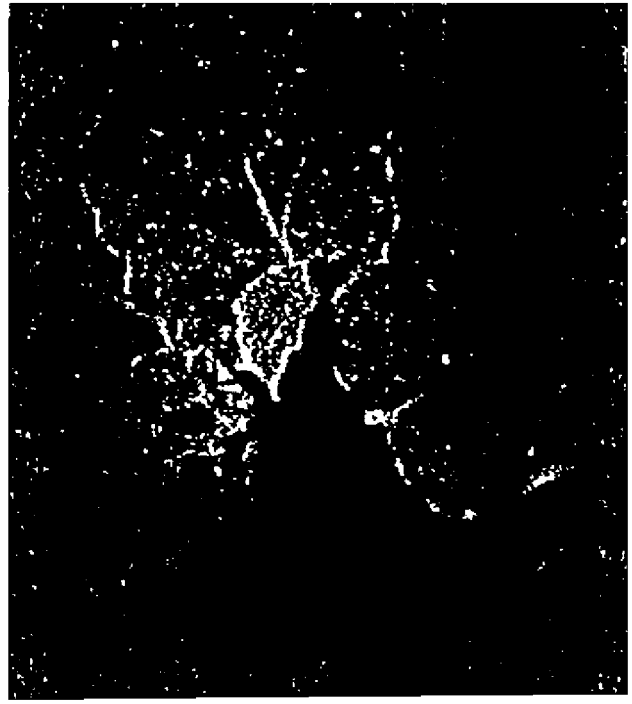

2) An rgs-CaM transgenic line is disabled for virus-induced gene silencing. To directly test if the rgs-CaM transgenic line is altered in the regulation of post-transcriptional gene silencing, we use a virus-induced gene silencing (VIGS) assay. This assay is well established (Baulcombe, 1999; Jones et al., 1998; Ruiz et al., 1998) and has been used successfully in our lab (Anandalakshmi et al., 1998). In this assay, a transgenic plant line expressing high levels of GFP is infected with a PVX vector expressing the GFP sequence (other reporter genes could be used so long as the gene is the same in the transgenic line and in the viral vector). The PVX-GFP replicates and moves systemically through the plant expressing high levels of GFP in leaves invaded early in the infection. The infection process triggers VIGS, a kind of post-transcriptional gene silencing. First the GFP transgene is silenced locally, and then throughout the upper part of the plant. Finally, very late in the infection, the viral vector (PVX-GFP) becomes silenced and is eliminated from the plant. At this point, in the absence of the viral trigger, the GFP transgene turns back on. We have previously shown that P1/HC-Pro interferes with VIGS in this system (Anandalakshmi et al., 1998). To demonstrate the effect of rgs-CaM in the same system, we cross an rgs-CaM expressing line (line 19, an rgs-CaM line with a pronounced phenotype, a primary transformant as described in Example 2) with a line expressing high levels of GFP (line 16C, the kind gift of D. Baulcombe, Sainsbury labs, Norwich, UK) to produce plants hemizygous for both the GFP and rgs-CaM transgenes. Plants from both lines are infected with PVX-GFP and are capable of supporting replication and spread of this virus based on local infection foci and systemic symptoms. The hemizygous 16C GFP plants (without the rgs-CaM transgene) become completely silenced for the GFP transgene at about ten days post-inoculation with PVX-GFP (and therefore the upper part of the plant fluoresces red under UV light due to the presence of chlorophyll rather than green as it does in the presence of GFP; FIG. 4A), as well as by a dramatic reduction in both GFP-transgene RNA and PVX-GFP viral RNA (data not shown). In contrast, plants hemizygous for both the GFP and rgs-CaM transgenes fail to silence when infected with PVX-GFP and continue to fluoresce green under long wave UV light (FIG. 4B). This is a direct demonstration that the rgs-CaM transgenic line is deficient in PTGS.

Figure 5:
FIG. 5. Reversal of PTGS by infection with PVX vector expressing rgs-CaM. (A) Agrosilenced GFP transgenic line infected with PVX control vector remains silenced; (B) Agrosilenced GFP transgenic line infected with PVX-rgs-CaM shows reversal of GFP silencing.
Figure 5:
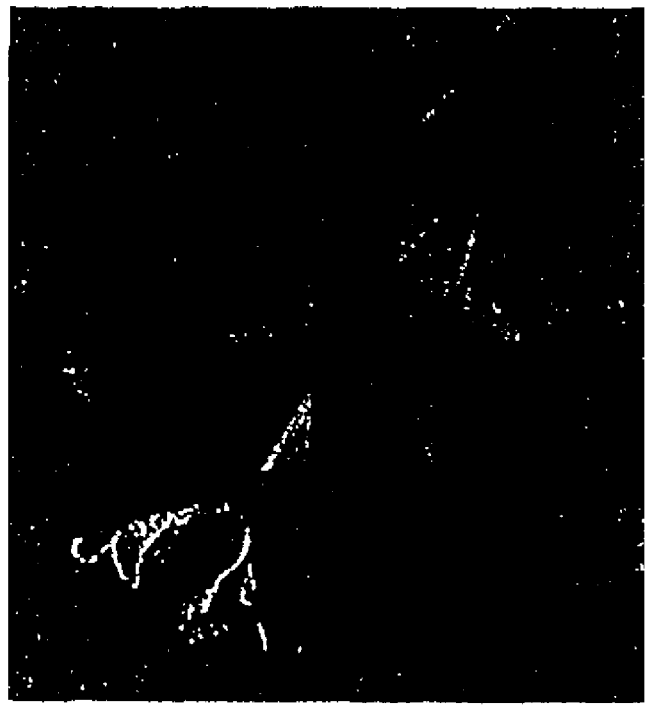

3) rgs-CaM reverses gene silencing when expressed from a PVX vector. To further demonstrate the role of rgs-CaM in regulating gene silencing, we employ a reversal of silencing assay described by Brigneti et al. (1998). In this approach, an *N. benthamiana* transgenic line (line 16C) expressing high levels of green fluorescent protein (GFP) is post-transcriptionally silenced by infiltrating the leaves with *Agrobacterium tumefaciens* carrying a vector that also expresses GFP. The *Agrobacterium* does not move from the inoculated leaf, but it induces PTGS of the GFP transgene locally, and then the GFP silencing spreads systemically through the plant until it is completely silenced. The GFP silencing in these plants can be reversed by infection with a PVX vector expressing a viral suppressor of silencing such as the potyviral HC-Pro or the cucumber mosaic virus 2a gene product (Brigneti et al., 1998). We silence the GFP plants by Agro-infiltration and then infect them with potato virus X carrying either wild-type HC-Pro (PVX-HC), a mutant inactive version of HC-Pro (PVX-noHC), or the rgs-CaM cDNA sequence (PVX-rgs-CaM). Plants infected with each of these viruses develop symptoms typical of the particular PVX vector (a mild mosaic pattern on leaves for PVX-rgs-CaM and PVX-noHC; a systemic necrosis for PVX-HC). The plants infected with PVX-noHC remain silenced for the GFP transgene (and therefore red under UV light, FIG. 5A). In contrast, plants infected with PVX-rgs-CaM show a reversal of the GFP silencing in the systemically infected portion of the previously silenced plant (areas of green in the red background, FIG. 5B). This reversal of silencing is typical of viral suppressors of silencing expressed from PVX (Brigneti et al., 1998) and is observed in the portions of silenced plants systemically infected with PVX-HC (data not shown). This result is consistent with the VIGS experiment described above and confirms that rgs-CaM is a cellular regulator of PTGS.

EXAMPLE 4

The ability of rgs-CaM over expressing transgenic plants to suppress transgene-induced gene silencing is demonstrated in *Agrobacterium* infiltration studies. A *Nicotiana benthamiana* transgenic line expressing both rgs-CaM and green fluorescent protein (GFP) or a control line expressing only the GFP transgene are infiltrated with a culture of *Agrobacterium* that also expresses the GFP transgene. Silencing of the GFP transgene in control plants is apparent in the region of local infiltration within a few days. Within two weeks this transgene-indued gene silencing moves throughout the upper part of the plant resulting in complete systemic silencing of the plant. In contrast, the rgs-CaM-expressing plants fail to silence in response to infiltration with *Agrobacterium*, or silencing occurs initially in a small local area but fails to spread efficiently. This result indicates that rgs-CaM is a suppressor of transgene induced gene silencing.

EXAMPLE 5

In order to determine whether the booster sequence will function to enhance expression of a stably incorporated transgene, the present Example may be conducted. A plant is first transformed by any mode of stable transformation with an endogenous plant gene for the purpose of over expressing that particular gene. A portion of the transformants are cosuppressed for the introduced gene and would fail to express gene product. These cosuppressed plants are then crossed with a plant stably transformed with the booster sequence, such as the transformants described in Example 2. The offspring of the cross express the previously silenced (cosuppressed) introduced endogenous gene.

EXAMPLE 6

The following Example describes the present method being utilized to express high levels of an endogenous gene product. A plant stably transformed with one or more copies of the booster sequence such as the rgs-CaM transformed plants described in Example 2 herein is subsequently transformed with an additional copy or additional copies of an endogenous gene for the purpose of overexpressing that gene product. The transformants display high levels of expression of the introduced gene product and/or reduced numbers of cosuppressed offspring that fail to express the gene product.

There are several other examples of transgene-induced post-transcriptional silencing where the booster sequence is expected to interfere with gene silencing and thereby boost expression. Two examples of such lines are currently being assayed by crossing with the P1/HC-Pro expressing transgenic lines and assaying for reversal of gene silencing. These silenced lines were both constructed in France at the INRS in the lab of Herve Vaucheret.

Transgenic line 475-2.1 is a tobacco transgenic line and is post-transcriptionally silenced for both transgene encoded and endogenous nitrite reductase (Nii) genes and has been previously described (J. C. Palauqui, T. Elmayan, F. Dorlhac de Borne, P. Crete, C. Charles and H. Vaucheret (1996) "Frequencies, Timing, and Spatial Patterns of Co-suppression of Nitrate Reductase and Nitrite Reductase in Transgenic Tobacco Plants," *Plant Physiol.* 112:1447–1456).

Transgenic line 30-18.9 is a tobacco transgenic line and is post-transcriptionally silenced for both transgene encoded and endogenous nitrate reductase (Nia) genes and has been previously described (J. C. Palauqui and H. Vaucheret (1995) "Field Trial Analysis of Nitrate Reductase Co-suppression: A Comparative Study of 38 Combinations of Transgene Loci," *Plant Mol. Biol.* 29:149–159).

EXAMPLE 7

Transgenic tobacco plants (*Nicotiana tabacum*) expressing the rgs-CaM sequence and control tobacco plants of that same variety are crossed with transgenic tobacco plants expressing a replicating RNA comprising a portion of the genomic RNA of potato virus X (PVX) with the uidA reporter gene inserted in place of the PVS coat protein gene (transgenic line 155; described by Angell (1997) *EMBO J.* 12:3675–3684). The expression of the betaglucuronidase (GUS) encoded by the uidA gene in the 155 line is monitored in each of the crosses by histochemical staining as described by Anandalakshmi et al. (1998) *Proc. Natl. Acad. Sci. USA* 95:13079–13084. The offspring of the cross between line 155 and the nontransformed control plants display little of the blue staining caused by GUS activity in this assay, indicating that the plants remain silenced in the hemizygous state. In contrast, the offspring of the cross of line 155 and rgs-CaM transformed lines display an intense blue stain after only a short incubation. This result indicates that silencing of PVS-GUS is reversed in the presence of rgs-CaM expression and suggests that the level of expression provided by the combination of the two transgenes is unexpectedly high. GUS activity levels are measured in offspring by a quantitative fluorometric enzyme assay as described by Jefferson (1987) *Plant Molecular Biology Reporter* 5:387–405. GUS activity in offspring of the cross of line 155 and the nontransformed control plants is low. In contrast, GUS activity in the offspring of the cross of line 155 and rgs-CaM transformants is exceptionally high as compared to those in offspring of the control cross or in conventional GUS-expressing transgenic lines such as line T19 (described in English et al. (1996) *Plant Cell* 8:179–188). GUS activity levels in the line 155/rgs-CaM combination are at least about two orders of magnitude higher than previously observed in transgenic plants.

EXAMPLE 8

In this example, the ability of the rgs-CaM sequence to reverse PTGS and produce enhanced expression is tested in another line (line 163; comprising the PVX genome with the uidA reporter gene inserted upstream of the PVX coat protein gene and under control of a repeated coat protein subgenomic promoter as described by Angell and Baulcombe (1997)). Line 163 differs from line 155 in several aspects: 1) line 163 contains the coat protein gene and produces coat protein, whereas line 155 has uidA inserted in place of the coat protein gene and therefore produces no coat protein; 2) the 25K triple block movement protein coding region of line 163 has a deletion that renders the RNA unable to move cell to cell, whereas this region is wild type in line 155. Since both the triple block proteins and the coat protein of PVX are required for movement of the viral RNA from cell to cell, both RNAs are confined to the cell where they are expressed, but for different reasons; 3) the level of GUS expression in line 163 is significantly lower than that in line 155 as previously shown by Angell and Baulcombe (1997). The lower levels of GUS activity in line 163 may be due to expression of the transgene from a repeated subgenomic promoter, to the production of coat protein, which may serve as a suppressor of viral replication, or to enhanced silencing triggered by the 163 line.

Line 163 is crossed with rgs-CaM transgenic plants and with control nontransformed plants of the same genetic background. The offspring of the cross between line 163 and the nontransformed control plants display little of the blue staining caused by GUS activity in this assay indicating that the plants remained silenced in the hemizygous state. In contrast, the offspring of the cross of line 163 and rgs-CaM transformants display an intense blue stain after only a short incubation, indicating that silencing of PVS-GUS is reversed in the presence of the viral sequence. GUS activity levels are measured as described in Example 1.

EXAMPLE 9

In this example, a transgenic line is produced comprising a replicating portion of the PVX genome similar to line 155, but with an endogenous plant gene such as phytoene desaturase in place of the coat protein gene (instead of the reporter gene encoding GUS as in line 155). This PVX-phytoene desaturase plant is crossed with the rgs-CaM transgenic line expressing the rgs-CaM suppressor of silencing and the offspring show reversal of PVX-phytoene desaturase silencing and enhanced expression of the phytoene desaturase gene product as compared to controls.

Other endogenous plant genes can be similarly expressed at enhanced levels by this method.

EXAMPLE 10

The present example sets forth an exemplary method for enhancing expression of an endogenous plant gene or a foreign gene (or a portion of a foreign or endogenous gene) that has been introduced to a plant as a fusion to a viral protein expressed from a viral vector. A viral vector expressing a foreign gene or an endogenous plant sequence as a fusion to the coat protein of the virus, such as the vector described in Sugiyama, Hamamoto, Takemoto, Watanabe, Okada (1995) "Systematic Production of Foreign Peptides on the Particle Surface of Tobacco Mosaic Virus," *FEBS Lett.* 359:247–250, is one such example. The viral vector may be used to infect a transgenic plant host that supplies the booster sequence via expression from stably incorporated DNA copies of said booster sequence, for example the rgs-CaM transgenic tobacco plants described herein (Example 2). The expression of the foreign peptides fused to the viral coat protein is enhanced as compared to expression of the foreign peptides in plants not comprising the rgs-CaM booster sequence.

Other gene product-producing vectors to which the presently described booster sequence could be supplied include those described in Hamamoto et al. (1993) *Bio/Technology* 11:930–932 and Takamatsu et al. (1990) *FEBS Lett.* 269:73–76.

EXAMPLE 11

The effect of rgs-CaM expression on transgene induced gene silencing is further examined using another transgenic line exhibiting a gene silencing phenotype. In this example, the silenced line (line 106-14) is crossed with rgs-CaM expressing lines or control plants, and plants from the F1 generation are then assayed for expression of the previously silenced gene.

The transgenic line 106-14 was constructed at NC State University and contains over 100 copies of the uidA gene under control of the cauliflower mosaic virus promoter and flanked by matrix attachment regions that are reported to interfere with transcriptional gene silencing. These plants express very high levels of GUS activity as seedlings and then silence developmentally, so that older plants fail to express detectable levels of GUS activity and are resistant to PVX-GUS. Developmental silencing is characteristic of post-transcriptional silencing. Line 106-14 is crossed with an rgs-CaM expressing line, and the offspring are susceptible to PVX-GUS and express high levels of GUS activity even in mature flowering plants. In contrast, offspring of control crosses with nontransformed tobacco (cv xanthi) and vector-only transformed tobacco (cv havana 425) fail to produce detectable GUS activity in leaves of mature plants.

This result is another example of the ability of the booster sequence to interfere with gene silencing and thereby boost expression of a gene product from a transgene.

EXAMPLE 12

In certain systems it is desirable to induce PTGS to prevent expression of endogenous genes and thereby cause a desired phenotype in the plant. However, it is known in the art that silencing is not always complete, and expression of the target sequence desired to be silenced occurs at reduced but yet still undesirable levels. In other cases, gene silencing is reversed, for example, in some instances of viral infection where HC-Pro produced by the viral pathogens has been shown to reverse gene silencing in infected plants. Advantageously, the rgs-CaM booster sequence can be modified using known techniques such as site-directed mutagenesis, synthetic construction of variant sequences, or Bal31 exonuclease to cause deletions or mutations of the sequence to yield polynucleotides which encode variant rgs-CaM peptides that retain the ability to interact with HC-Pro, yet fail to mediate the interference with gene silencing. Plants into which such polynucleotides are introduced and expressed have more stable PTGS even in the face of viral infection.

Using the methods of the invention, increased expression of target sequences can be realized. Thus, plants and plant cells and tissues having enhanced production of plant proteins, transgenic proteins, and the like can be produced. Because co-suppression is a general phenomenon in plants, the methods have wide applicability in all plants.

All publications and patent applications mentioned in the specification are indicative of the level of those skilled in the art to which this invention pertains. All publications and patent applications mentioned in the specification are herein incorporated by reference to the same extent as if each individual publication or patent application was specifically and individually indicated to be incorporated by reference, each to the extent not inconsistent with the explicit teachings set forth herein.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Anandalakshmi, R., Pruss, G. J., Ge, X., Marathe, R., Mallory, A. C., Smith, T. H. and Vance, V. B. (1998) "A viral suppressor of gene silencing in plants," *Proc. Natl. Acad. Sci. USA* 95:13079–13084.

Al-Kaff, N. S., Covey, S. N., Kreike, M. M., Page, A. M., Pinder, R. & Dale, P. J. (1998) "Transcriptional and post transcriptional plant gene silencing in response to a pathogen," *Science* 279:2113–2115.

Baulcombe, D. C. (1999) "Fast forward genetics based on virus-induced gene silencing," *Gurr. Opin. Plant Biol.* 2:109–113.

Bingham, P. M. (1997) "Cosuppression comes to the animals," *Cell* 90:385–387.

Brigneti, G., Voinnet, O., Li, W. -X., Ji, L. -H., Ding, S. -W. and Baulcombe, D. (1998) "Viral pathogenicity determinants are suppressors of transgene silencing in *Nicotiana benthamiana*," *EMBO J.* 17:6739–6746.

Carrington et al. (1990) *EMBO. J.* 9:1347–1353.

Dearolf, C. R., Hersperger, E. and Sheam A. (1988) "Developmental consequences of awdb3, a cell-autonomous lethal mutation of Drosophila induced by hybrid dysgenesis," *Dev. Biol.* 129:159–168.

de la Rosa, A., Williams, R. L. and Steeg, P. S. (1995) "Nm23/nucleoside diphosphate kinase: toward a structural and biochemical understanding of its biological functions," *Bioassays* 17:53–62.

Depicker, A. and Van Montagu, M. (1997) "Post-transcriptional gene silencing in plants," *Gurr. Opin. Cell Biol.* 9:373–382.

Engel, M., Seifert, M., Theisinger, B., Seyfert, U., and Welter, C. (1998) "Glyceraldehyde3-phosphate dehydrogenase and NM23-HI/nucleoside diphosphate kinase A. Two old enzymes combine for the novel Nm23 protein phosphotransferase function," *J. Biol. Chem.* 273:20058–20065.

Fire, A., Xu, S., Montgomery, M. K., Kostas, S. A., Driver, S. E. and Mello, C. C. (1998) "Potent and specific genetic interference by double stranded RNA in *Caenorhabditis elegens.*," *Nature* 391:806–811.

Fire, A., *Trends Genet.* 15, 358 (1999).

Grant, S. (1999) "Dissecting the mechanisms of post transcriptional gene silencing: Divide and conquer," *Cell* 96:303–306.

Howlett, A. R., Peterson, O. W., Steeg, P. S., and Bissell, M. J. (1994) "A novel function for the nm23-H1 gene: overexpression in human breast carcinoma cells leads to the formation of basement membrane and growth arrest," *J. Natl. Cancer Inst.* 86:1838–1844.

Jones, A. L., Thomas, C. L. and Maule, A. J. (1998) "De novo methylation and cosuppression induced by a cytoplasmically replicating plant RNA virus," *EMBO J.* 17:6385–6393.

Kasschau, K. D. and Camngton, J. C. (1998) "A counter-defensive strategy of plant viruses: Suppression of post transcriptional gene silencing." *Cell* 95:461–470.

Kennerdell, J. R. and Carthew, R. W. (1998) "Use of dsRNA-mediated genetic interference to demonstrate that frizzled and frizzled 2 act in the wingless pathway," *Cell* 95:1017–1026.

Kumagai, M. H., Donson, J., Della-Cioppa, G., Harvey, D., Hanley, K., and Grill, L. K. (1995) "Cytoplasmic inhibition of carotenoid biosynthesis with virus-derived RNA," *Proc. Natl. Acad. Sci USA* 92:1679–1683.

Matzke, M. A. and Matzke, A. J. M. (1995) "Homology-dependent gene silencing in transgenic plants: what does it really tell us," *Trends in Genetics II*, 1–3.

Metzlaff, M., O'Dell, M., Cluster, P. D., and Flavell, R. B. (1997) "RNA-mediated RNA degradation and chalcone synthase A silencing in Petunia," *Cell* 88:845–854.

Montgomery, M. K. and Fire, A. (1998) "Double stranded RNA as a mediator in sequence specific genetic silencing and co-suppression," *Trends Genet.* 14:255–258.

Palauqui, J. C. and H. Vaucheret (1995) "Field Trial Analysis of Nitrate Reductase Co-suppression: A Comparative Study of 38 Combinations of Transgene Loci," *Plant Mol. Biol.* 29:149–159.

Palauqui, J. C., T. Elmayan, F. Dorlhac de Borne, P. Crete, C. Charles and H. Vaucheret (1996) "Frequencies, Timing, and Spatial Patterns of Co-suppression of Nitrate Reductase and Nitrite Reductase in Transgenic Tobacco Plants," *Plant Physiol.* 112:1447–1456.

Postel, E. H., Berbench, S. J., Flint, S. J., and Ferrone, C. A. (1993) "Human c-myc transcription factor PuF identified as nm-23-H2 nucleoside diphosphate kinase, a candidate suppressor of tumor metastasis," *Science* 261:478–480.

Pruss, G., Ge, X., Shi, X. M., Camngton, J. C., and Vance, V. B. (1997) "Plant viral synergism: the potyviral genome encodes a broad-range pathogenicity enhancer that transactivates replication of heterologous viruses," *Plant Cell* 9:1–11.

Ratcliff, F., Harrison, B., and Baulcombe, D. (1997) "A similarity between viral defense and gene silencing in plants," *Science* 276:1558–1560.

Ramano, N. and Macmo, C. (1992) "Quelling: transient inactivation of gene expression in *Neurospora crassa* by transformation with homologous sequences," *Mol. Microbiol.* 6:3343–3353.

Rudd and Franklin-Tong, 1999.

Ruiz, M. T., Voinnet, O., and Baulcombe, D. C. (1998) "Initiation and amintenance of virus-induced gene silencing," *Plant Cell* 10:937–946.

Rumz, F., Vayssie, L., Klotz, C., Sperling, L., and Madeddu, L. (1998) "Homology-dependent gene silencing in Paramecium," *Mol. Biol. Cell* 9:931–943.

Sharp, P. A., *Genes Dev.*, 13, 139 (1999).

Sharp, P. A. and P. D. Zamore, *Science* 287,2431 (2000).

Snedden and Hillel, 1999.

Vance, V. B. (1991) "Replication of potato virus X RNA is altered in coinfections with potato virus Y," *Virology* 182:486–494.

Vance, V. B., Berger, P. H., Canington, J. C., Hunt, A. G., and Shi, X. M. (1995) "5' proximal potyviral sequences mediate potato virus X/potyviral synergistic disease in transgenic tobacco," *Virology* 206:583–590.

Waterhouse, P. M., Graham, M W. and Wang, M. (1998) Virus resistance and gene silencing in plants can be induced by simultaneous expression of sense and antisense RNA," *Proc. Natl. Acad. Sci. USA* 95:13959–13964.

Wianny, F. and M. Zernicka-Goetz, *Nature Cell. Biol.* 2, 70 (2000).

---

What is claimed is:

1. In a method of expressing a foreign gene or an endogenous plant gene that has been introduced into plant cells, plant protoplasts, or whole plants, the improvement comprising the supplying of a booster sequence comprising a polynucleotide encoding an rgs-CaM protein to said plant cells, plant protoplasts, or whole plants so as to suppress post-transcriptional gene silencing (PTGS) of the expression of said foreign gene or endogenous plant gene as compared to said expression in said plant cells, plant protoplasts, or whole plants without said booster sequence; wherein said polynucleotide comprises a nucleotide sequence selected from the group consisting of:

(a) the nucleotide sequence set forth in SEQ ID NO:1;

(b) and a nucleotide sequence that encodes the polypeptide set forth in SEQ ID NO:2.

2. The method of claim 1, wherein said introduced gene is a foreign gene that was not naturally occurring in said plant cells, plant protoplasts, or whole plants prior to being introduced therein.

3. The method of claim 1, wherein said introduced gene is an endogenous plant gene that was naturally occurring in said plant cells, plant protoplasts, or whole plants prior to being introduced as an additional copy or additional copies of the endogenous gene.

4. The method of claim 1, wherein said booster sequence is not fused to said foreign gene or said endogenous plant gene.

5. The method of claim 1, wherein said booster sequence is fused to said foreign gene or said endogenous plant gene.

6. The method of claim 1, wherein said foreign gene or endogenous plant gene is introduced via a viral expression vector and said booster sequence is supplied by expression from the same viral vector.

7. The method of claim 1, wherein said foreign gene or endogenous plant gene is introduced via a viral expression vector and said booster sequence is supplied by expression of one or more DNA copies of said booster sequence stably incorporated into the plant's genome.

8. The method of claim 1, wherein said booster sequence is expressed from a transient expression system.

9. The method of claim 1, wherein a two-component viral vector system is used with one viral component expressing said booster sequence a the other viral component expressing said introduced gene.

10. The method of claim 1, wherein said foreign gene or endogenous plant gene is introduced to said plant genome via any mode of stable transformation of one or more copies of said introduced gene, and said booster sequence is supplied prior to introduction of said foreign gene or endogenous plant gene via stable transformation procedures.

11. The method of claim 1, wherein said foreign gene or endogenous plant gene is introduced to said plant genome via any mode of stable transformation of one or more copies of said introduced gene into the plant genome, and said booster sequence is supplied during the process of introduction of said foreign gene or endogenous plant gene via stable transformation procedures.

12. The method of claim 1, wherein said foreign gene or endogenous plant gene is introduced into said plant genome via any mode of stable transformation of one or more copies of said introduced gene into the plant genome, and said booster sequence is supplied after introduction of said foreign gene or endogenous plant gene via stable transformation procedures.

13. An isolated polynucleotide encoding a polypeptide, wherein said polynucleotide comprises a nucleotide sequence selected from the group consisting of:

(a) the nucleotide sequence set forth in SEQ ID NO:1;

(b) and a nucleotide sequence that encodes the polypeptide set forth in SEQ ID NO:2.

* * * * *

UNITED STATES PATENT AND TRADEMARK OFFICE
CERTIFICATE OF CORRECTION

PATENT NO. : 6,972,349 B1  
APPLICATION NO. : 09/711334  
DATED : December 6, 2005  
INVENTOR(S) : Vance It is certified that error appears in the above-identified patent and that said Letters Patent is hereby corrected as shown below:

<u>Title page,</u>
Item [56], References Cited, OTHER PUBLICATIONS,
"Wiammy, F." reference, should read -- Wianny, F. and M. Zernick-Goetz (2000) "Specific inter- --.

<u>Column 28,</u>
Line 36, should read -- said booster sequence and the other viral component express- --.

Signed and Sealed this

Eleventh Day of July, 2006

JON W. DUDAS  
*Director of the United States Patent and Trademark Office*

SEQUENCE LISTING

```
<160> NUMBER OF SEQ ID NOS: 2

<210> SEQ ID NO 1
<211> LENGTH: 948
<212> TYPE: DNA
<213> ORGANISM: Nicotiana tabacum

<400> SEQUENCE: 1
acaaaagctg agctccaccg cggtgcgccg ctctagaact agtgatcccc cggctgcaga      60
attcgcacga gaagttttcc ttttagcttc aagttcaacc cttttcacac ttattgtatt     120
ctacttacat atctcaaatt atcttgaaat taaaggaaaa aaccagtcta agacttacta     180
gtttagttgt tatacgtgca acatgtgcat ggaatcagtt tctgtaccta gtgttgaaaa     240
caaatcttat ttctcaagat taaggaagag gttttcactc aaaaaggcaa cgacgactac     300
aacaacaaca actattacta ctgattatct ttcgatgagt agtagtagca aaagtaataa     360
tagtggcgag ttagagaggg tatttacata ctttgacgag aatggagatg gaaaagtgtc     420
accggctgag ctcaggaggt gtgtgaaggc gttaggaggc gaactgacgg tggaggaggc     480
ggagatggcg gtgaggctat cggattccga cggggatgga ttgttgggtt tggaggattt     540
tacaaaacta atggaaggaa tggaagagga gagaaataag gagagtgaat tgataggagc     600
atttggaatg tatgaaatgg aggggagtgg ctacattact cctaagagtt tgaagatgat     660
gttgagtcga ctcggtgagt caacttccat tgataactgc aaagctatga ttcagagatt     720
tgatatcaat ggagatggag ttctcaactt tgatgagttc aaagctatga tgacaagtta     780
actagatttc aacacacaaa tagtgtaatt atacatgtac ataattcttt ggccttgggc     840
agcttgttgt ttgtttcttg ataaaaagat aaataaattc tgattaatcg ttaaaaaaaa     900
aaaaaaaaaa aactcgaggg ggttcccgta cccaatctgc cctatagt                  948

<210> SEQ ID NO 2
<211> LENGTH: 192
<212> TYPE: PRT
<213> ORGANISM: Nicotiana tabacum

<400> SEQUENCE: 2

Met Cys Met Glu Ser Val Ser Val Pro Ser Val Glu Asn Lys Ser Tyr
1               5                   10                  15

Phe Ser Arg Leu Arg Lys Arg Phe Ser Leu Lys Lys Ala Thr Thr Thr
            20                  25                  30
```

-continued

```
Thr Thr Thr Thr Thr Ile Thr Thr Asp Tyr Leu Ser Met Ser Ser Ser
         35              40              45

Ser Lys Ser Asn Asn Ser Gly Glu Leu Glu Arg Val Phe Thr Tyr Phe
     50              55              60

Asp Glu Asn Gly Asp Gly Lys Val Ser Pro Ala Glu Leu Arg Arg Cys
 65              70              75                       80

Val Lys Ala Val Gly Gly Glu Leu Thr Val Glu Glu Ala Glu Met Ala
             85              90                       95

Val Arg Leu Ser Asp Ser Asp Gly Asp Gly Leu Leu Gly Leu Glu Asp
             100             105             110

Phe Thr Lys Leu Met Glu Gly Met Glu Glu Arg Asn Lys Glu Ser
         115             120             125

Glu Leu Ile Gly Ala Phe Gly Met Tyr Glu Met Glu Gly Ser Gly Tyr
     130             135             140

Ile Thr Pro Lys Ser Leu Lys Met Met Leu Ser Arg Leu Gly Glu Ser
145             150             155             160

Thr Ser Ile Asp Asn Cys Lys Ala Met Ile Gln Arg Phe Asp Ile Asn
             165             170             175

Gly Asp Gly Val Leu Asn Phe Asp Glu Phe Lys Ala Met Met Thr Ser
             180             185             190
```